United States Patent
Stahl

(10) Patent No.: US 10,569,006 B2
(45) Date of Patent: Feb. 25, 2020

(54) DEVICE FOR MONITORING A VESSEL OPENING FOR AN EXTRACORPOREAL BLOOD TREATMENT DEVICE AND METHOD FOR MONITORING A VESSEL OPENING

(71) Applicant: FRESENIUS MEDICAL CARE DEUTSCHLAND GMBH, Bad Homburg (DE)

(72) Inventor: Thomas Stahl, Esselbach (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 198 days.

(21) Appl. No.: 15/319,806

(22) PCT Filed: Jun. 17, 2015

(86) PCT No.: PCT/EP2015/063619
§ 371 (c)(1),
(2) Date: Dec. 19, 2016

(87) PCT Pub. No.: WO2015/197450
PCT Pub. Date: Dec. 30, 2015

(65) Prior Publication Data
US 2017/0136171 A1 May 18, 2017

(30) Foreign Application Priority Data

Jun. 25, 2014 (DE) .................... 10 2014 009 388

(51) Int. Cl.
*A61M 1/36* (2006.01)
*A61M 39/02* (2006.01)

(52) U.S. Cl.
CPC ...... *A61M 1/3656* (2014.02); *A61M 39/0247* (2013.01); *A61M 2039/0258* (2013.01);
(Continued)

(58) Field of Classification Search
CPC ............ A61M 1/3656; A61M 2205/15; A61M 2205/18; A61M 2205/3592;
(Continued)

(56) References Cited

U.S. PATENT DOCUMENTS 7,147,615 B2  12/2006  Wariar et al.
8,348,850 B2 *  1/2013  Frinak ................ A61M 1/3655
                                                    600/485
(Continued)

FOREIGN PATENT DOCUMENTS

CN          1564477 A    1/2005
CN       101959485 A    1/2011
(Continued)

OTHER PUBLICATIONS

English Abstract of CN102438337A.*
(Continued)

*Primary Examiner* — Leslie R Deak
(74) *Attorney, Agent, or Firm* — Kilyk & Bowersox, P.L.L.C.

(57) ABSTRACT

The invention relates to a device A for monitoring a vessel opening for an extracorporeal blood treatment device B with an extracorporeal blood circulation (I), which has an arterial blood line (20) with an arterial cannula (19) and a venous blood line (21) with a venous cannula (22). Moreover, the invention relates to an arrangement with a device A for monitoring a vessel opening and an extracorporeal blood treatment device B, and a method for monitoring a vessel opening during an extracorporeal blood treatment. The monitoring device A comprises a sensor (1) for detecting at least one physical variable, which is characteristic for the state of the vessel opening, and an evaluation apparatus (7), connected to the sensor (1) by way of a connection cable (6), for producing signals characteristic for the state of the vessel opening. The evaluation apparatus (7) has a data transmission unit (38) for establishing a wireless connection between the evaluation apparatus (7) and the blood treatment device B. The evaluation apparatus (7) is distinguished by a control unit (39) configured in such a way that an interruption in the wireless connection between the evaluation apparatus (7)

(Continued)

Figure 1:
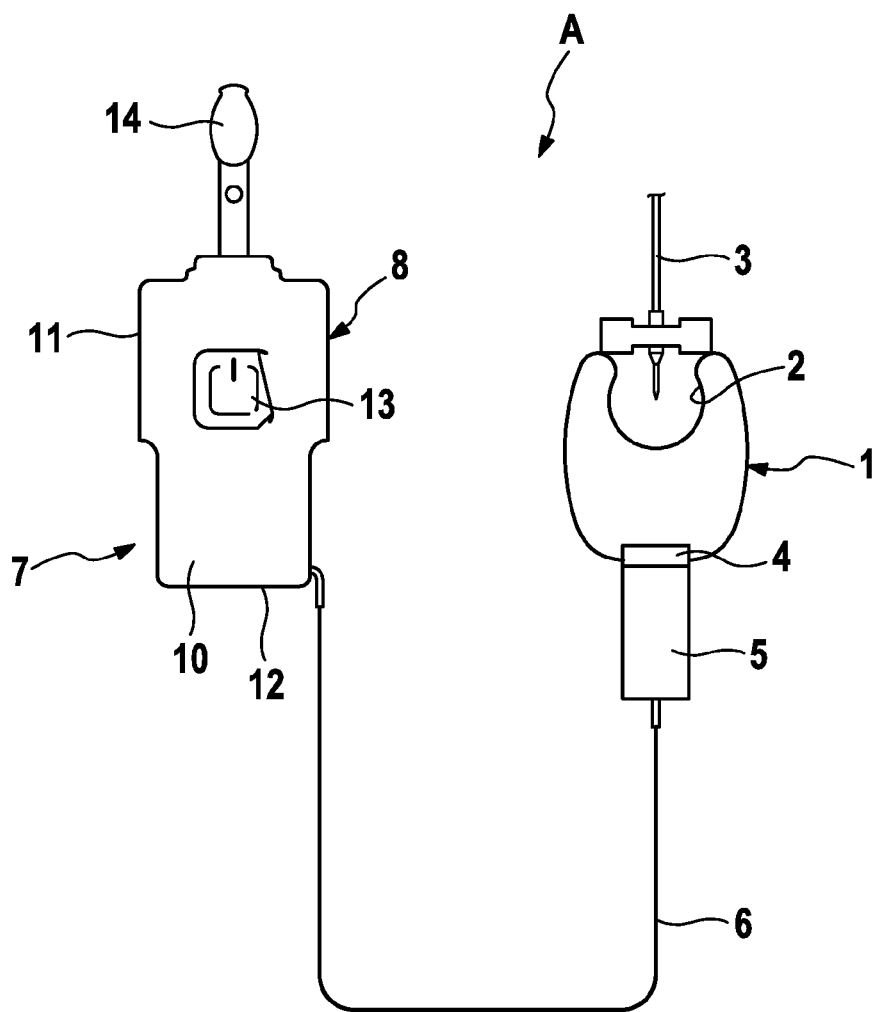

and the blood treatment device B is identified, for example if the patient were to lie on the evaluation apparatus (7). Moreover, the monitoring device A has a signal unit (40), which has a vibration transducer (40A) which causes the housing (8) of the evaluation apparatus (7) to vibrate when the wireless connection is interrupted.

12 Claims, 2 Drawing Sheets

(52) U.S. Cl.
CPC .............. *A61M 2039/0267* (2013.01); *A61M 2039/0273* (2013.01); *A61M 2039/0276* (2013.01); *A61M 2205/13* (2013.01); *A61M 2205/15* (2013.01); *A61M 2205/18* (2013.01); *A61M 2205/3317* (2013.01); *A61M 2205/3379* (2013.01); *A61M 2205/3523* (2013.01); *A61M 2205/3569* (2013.01); *A61M 2205/3592* (2013.01); *A61M 2205/587* (2013.01); *A61M 2205/8206* (2013.01)

(58) Field of Classification Search
CPC .. A61M 2039/0258; A61M 2039/0267; A61M 39/0247
See application file for complete search history.

(56) References Cited

U.S. PATENT DOCUMENTS

| | | | |
|---|---|---|---|
| 8,398,575 | B1 | 3/2013 | McCall |
| 2005/0038325 | A1 | 2/2005 | Moll |
| 2011/0046534 | A1 | 2/2011 | Gross |
| 2013/0090581 | A1* | 4/2013 | Yamazaki .......... A41D 19/0024 601/81 |
| 2014/0100519 | A1 | 4/2014 | Susi |
| 2015/0328389 | A1 | 11/2015 | Heppe |

FOREIGN PATENT DOCUMENTS

| | | |
|---|---|---|
| CN | 102438337 A * | 5/2012 |
| EP | 2117625 B1 | 11/2012 |
| EP | 2331212 B1 | 10/2013 |
| WO | 2011116943 A1 | 9/2011 |

OTHER PUBLICATIONS

International Search Report issued in corresponding International Patent Application No. PCT/EP2015/063619 dated Sep. 8, 2015 (3 pages).

The State of Intellectual Property Office of People's Republic of China Patent Office, Office Action for Chinese Patent Application No. CN201580033937.1 dated Aug. 31, 2018, with English-language Translation.

\* cited by examiner

DEVICE FOR MONITORING A VESSEL OPENING FOR AN EXTRACORPOREAL BLOOD TREATMENT DEVICE AND METHOD FOR MONITORING A VESSEL OPENING

This application is a National Stage Application of PCT/EP2015/063619, filed Jun. 17, 2015, which claims priority to German Patent Application No. 10 2014 009 388.3, filed Jun. 25, 2014, which are incorporated in their entireties by reference herein.

The invention relates to a device for monitoring a vascular access for an extracorporeal blood treatment device having an extracorporeal blood circuit which comprises an arterial blood line having an arterial cannula and a venous blood line having a venous cannula. In addition, the invention relates to an arrangement having a device for monitoring a vascular access and an extracorporeal blood treatment device, and to a method for monitoring a vascular access during extracorporeal blood treatment.

During the extracorporeal blood treatment, blood is taken from the patient via an arterial hose line having an arterial cannula, and is fed back to the patient via a venous hose line having a venous cannula. A cannula can be understood to be, for example, a puncture cannula, a dialysis needle or a needle. The extracorporeal blood treatment devices which have an extracorporeal blood circuit presuppose proper access to the patient. Examples of known extracorporeal blood treatment devices are dialysis devices and cell separators.

Although the vascular access is continuously monitored during the blood treatment, there is the fundamental risk of the cannula slipping out of the blood vessel of the patient without being noticed. In order to monitor the vascular access, various devices of different configurations are known which trigger immediate interruption of the extracorporeal blood circuit in the event of an improper vascular access.

WO 2011/116943 A1 discloses a device intended for monitoring a vascular access and having a sensor which detects a variable which is characteristic of the state of the vascular access. The sensor is designed as a pad which is placed onto the patient's skin at the puncture site. The sensor measures the moisture or the escape of fluid at the puncture site as the variable which is characteristic of the state of the vascular access. The sensor is connected via a connection cable to an evaluation unit, by means of which the sensor signal is evaluated. If blood escapes from the puncture site, an acoustic alarm is sounded and the blood treatment is interrupted.

A device for monitoring a vascular access during dialysis is also known from US 2005/0038325 A1. The monitoring device has a moisture sensor which is connected via a connection cable to an evaluation unit which comprises an alarm generator that sets off a vibrating alarm in the event of a faulty vascular access.

U.S. Pat. No. 8,398,575 B1 also describes a monitoring device comprising a moisture sensor and an evaluation unit which are interconnected via a cable. The evaluation unit also sets off a vibrating alarm in the event of a faulty vascular access. U.S. Pat. No. 8,348,850 B2 also proposes setting off a vibrating alarm in the event of a faulty vascular access so that the patient is woken up if they are asleep.

DE 43 29 898 A1 discloses a wireless medical diagnosis and monitoring apparatus which comprises a sensor and an evaluation unit. The sensor and the evaluation unit each comprise a data transmission unit, between which radio signals are transmitted, the transmitting power automatically being adapted to the local conditions. In order to protect the patient from electromagnetic radiation that is too high, the radio connection is monitored. When the transmitting power is too high, the radio connection is interrupted and an alarm is set off.

The object of the invention is to provide a device for monitoring a vascular access which is not linked to the extracorporeal blood treatment device via a cable and which, together with the blood treatment device, allows for the vascular access to be monitored with a high degree of safety. In addition, the object of the invention is to provide a method for monitoring a vascular access during extracorporeal blood treatment, which method, together with the blood treatment device, allows for the vascular access to be monitored with a high degree of safety even when the device for monitoring a vascular access is not linked to the blood treatment device via a cable.

These objects are achieved with the features of the independent claims. The dependent claims relate to advantageous embodiments of the invention.

The device according to the invention for monitoring a vascular access for an extracorporeal blood treatment device has a sensor for detecting at least one physical variable, which is characteristic of the state of the vascular access, and comprises an evaluation apparatus, which is connected to the sensor via a connection cable and comprises an evaluation unit. The evaluation unit, which evaluates the measured physical variable, generates signals which are characteristic of the state of the vascular access.

The signals which are characteristic of the state of the vascular access can be signals which signal an error-free and/or faulty vascular state, i.e. that the cannula is in the correct place or that the cannula has slipped out. In particular, the signal is a signal which signals a faulty state.

The sensor is attached at the puncture site, the cable-bound evaluation apparatus being arranged remote from the puncture site. The evaluation apparatus comprises a data transmission unit for producing a wireless connection between the evaluation apparatus and the blood treatment device, so that the evaluation apparatus is not linked to the blood treatment device via a cable. The wireless connection between the evaluation apparatus and blood treatment device can be a connection via radio signals or optical signals. If the wireless connection is established via radio signals, the transmitting power should be low in order to protect the patient from excessive electromagnetic radiation and/or to reduce the energy consumption so as to extend the operating time during battery operation. The blood treatment device and evaluation apparatus are associated uniquely with one another, for example by an operator confirming correct association within a predetermined time period. When the transmitting power is low, the wireless connection only exists in the immediate vicinity of the evaluation apparatus, and therefore no connection can be established to other blood treatment devices which are in the dialysis unit but not in the immediate vicinity of the evaluation apparatus.

In light of the relatively low transmitting power, the wireless connection between the evaluation apparatus and the blood treatment device can be interrupted during blood treatment, in that the patient comes to lie on the evaluation apparatus. If the patient is asleep during the blood treatment, they will not notice the radio connection being interrupted, and therefore the blood treatment is not interrupted and no alarm is set off when the cannula slips out.

The evaluation apparatus of the monitoring device according to the invention is characterised by a supervision unit which is configured to detect an interruption of the wireless connection between the evaluation apparatus and the blood treatment device. In addition, the monitoring device comprises a signalling unit which emits a signal if the supervision unit detects that the wireless connection has been interrupted. The signalling unit is characterised by a vibration signal generator which uses vibrations to signal that the wireless connection has been interrupted. The vibrations, which are transmitted to the body of the patient lying on the evaluation apparatus, cause the patient to wake up so that they can move and release the evaluation apparatus. This signalling of a disrupted connection between the apparatuses has to be differentiated from the actual alarm that is triggered when a faulty vascular access is determined. An alarm is directed in particular at the medical staff who can take appropriate counter-measures to bring the blood treatment device into a state that is safe for the patient, for example by stopping the blood pump and/or closing the venous and/or arterial hose clamp.

A preferred embodiment of the invention provides that the supervision unit is configured such that a conclusion is only made regarding an interruption of the wireless connection between the evaluation apparatus and the blood treatment device when the wireless connection is interrupted for a period of time that is longer than a predetermined period of time. This is intended to ensure that brief position changes of the patient do not immediately cause the interruption of the wireless connection to be signalled by vibrations.

In a preferred embodiment, the signals which are characteristic of the state of the vascular access are sent to the blood treatment device by a transmitting unit. A unidirectional connection is sufficient for the transmission of the data that is relevant for monitoring the vascular access. Alongside the transmitting unit, the preferred embodiment provides a receiving unit, by means of which confirmation signals are received by the blood treatment device in order to monitor the wireless connection. The supervision unit is preferably configured to detect when the receiving unit is not receiving a confirmation signal from the blood treatment device signalling the existence of the wireless connection. Since the evaluation apparatus sends the signals which are characteristic of the state of the vascular access to the blood treatment device at least at predetermined time intervals, a conclusion can be made regarding an interruption of the wireless connection even when the blood treatment device does not receive these signals. The blood treatment device can then send a signal to the evaluation apparatus signalling the interruption of the wireless connection.

The design of the sensor and the functional principle on which it is based is not important to the invention. In a preferred embodiment, the sensor is designed as a pad which is made of flexible material and is to be placed on the patient's skin. Preferably, the sensor comprises a moisture or liquid sensor as the sensor element, by means of which the escape of blood at the puncture site can be determined if the cannula has slipped out.

The vibrations should also be sufficiently strong to wake the patient even from a deep sleep. In order to generate a vibration signal that is as strong as possible, the vibration signal generator is preferably connected to a wall of the housing of the evaluation apparatus to which the vibrations are to be transmitted. The housing is preferably formed as a flat housing having a front wall and a rear wall and a narrow side wall, the vibration signal generator being connected to the front wall and/or the rear wall and the connection cable being guided out of the housing at the side wall. If the patient lies on the evaluation apparatus, their body will come to lie on the front or rear flat housing wall. Owing to the relatively large contact surface, the patient will feel the vibrations clearly.

The extracorporeal blood treatment device comprises a data transmission unit for producing a wireless connection between the blood treatment device and the evaluation apparatus, the data transmission unit of the evaluation apparatus and of the blood treatment device forming an interface which can be based on various standards. For example, the interface can operate according to the Bluetooth standard. However, the interface could also be an interface which functions using optical signals, although this is less suitable than an interface transmitting radio signals. The known interfaces provide corresponding transceiver units, via which data communication takes place.

The blood treatment device receives signals which are characteristic of the state of the vascular access, in particular a signal for a faulty vascular access. In a preferred embodiment, the blood treatment device comprises an alarm unit which is designed to generate an acoustic and/or optical alarm following receipt of a signal which is characteristic of a faulty vascular access. However, the evaluation apparatus can also have an alarm unit of this type. The blood treatment device can also comprise a signalling unit which is designed to generate an acoustic and/or an optical signal following interruption of the wireless connection, so that an interruption of the wireless connection is also signalled to the medical staff.

The blood treatment device can signal the interruption of the wireless connection after a certain time delay after the signalling by the evaluation apparatus. Preferably, first the evaluation apparatus sets off a vibration signal so that the patient can re-establish the wireless connection. The blood treatment device preferably only signals the interruption of the connection if the patient is not able to re-establish the connection within a predetermined time interval. This provides relief for the medical staff. It is possible, however, for the blood treatment device and the evaluation apparatus to signal the interruption of the connection at the same time. Preferably, the blood treatment device and the evaluation apparatus should be configured such that the time delay with which the blood treatment device reacts to the interruption of the connection can be predetermined by the medical staff.

Figure 2:
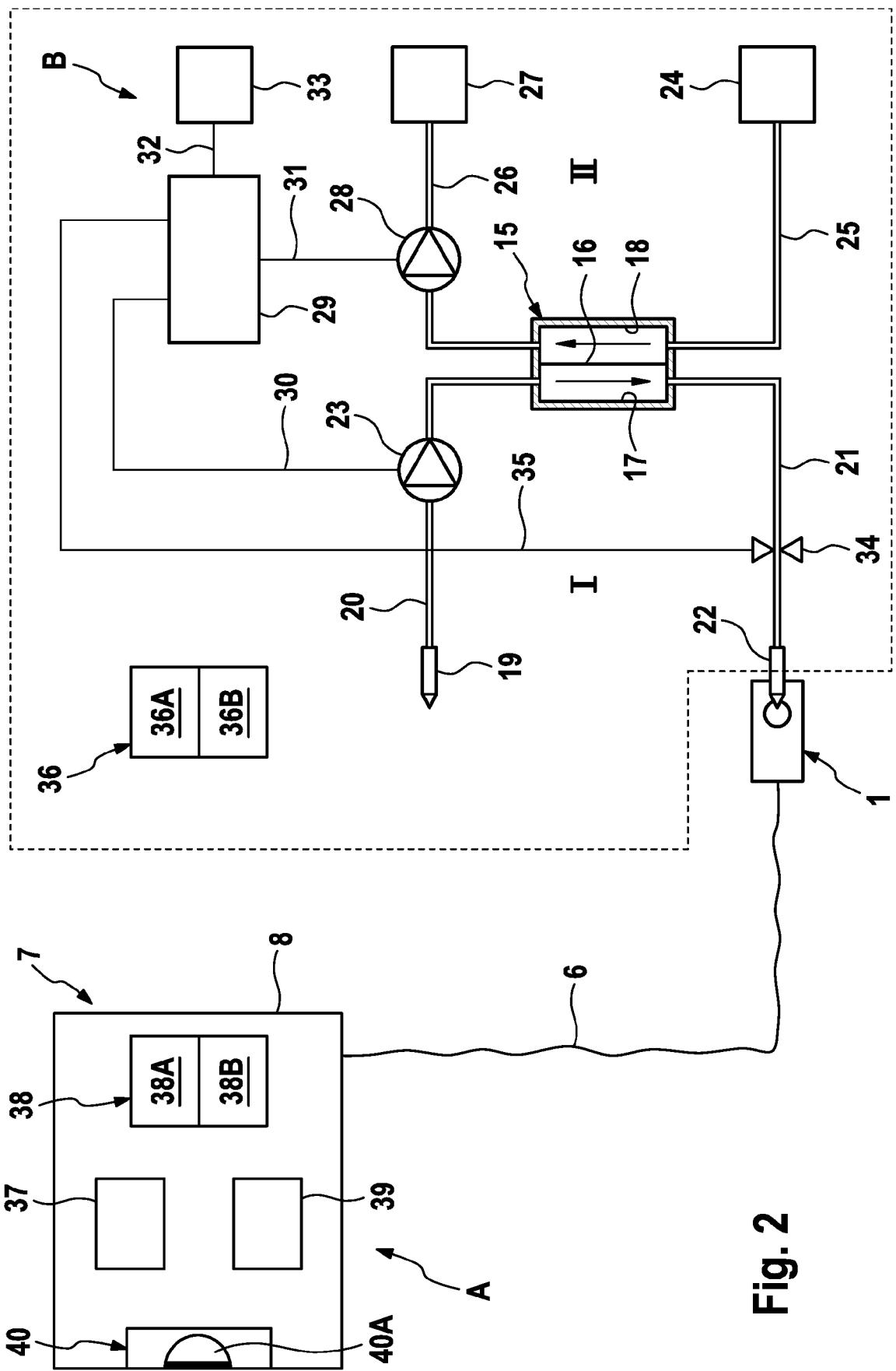

An embodiment of the invention is explained in more detail below with reference to the drawings, in which:

FIG. 1 is a plan view of the device according to the invention for monitoring a vascular access for a blood treatment device and FIG. 2 is a schematic view of the essential components of the device for monitoring a vascular access and of a blood treatment device.

FIG. 1 shows an embodiment of the device A according to the invention for monitoring a vascular access for a blood treatment device. The monitoring device A comprises a sensor 1 which is attached to the patient's skin at the puncture site. The sensor 1 is formed as a pad made of a flexible and absorbent material which comprises a cut-out 2 on one side for passing through a cannula 3. On the side opposite the cut-out, the sensor comprises a connection tab 4 for a connection clamp 5 of a connection cable 6, which leads to an evaluation apparatus 7.

The sensor 1 comprises a sensor element (not shown) which detects a variable which is characteristic of the state of the vascular access which can for example be the electrical resistance which changes if the pad comes into contact with blood. In order to measure the electrical resistance, the sensor element can for example be an electric wire loop.

The evaluation apparatus 7 comprises a flat housing 8 which has a front wall 10 and a rear wall 11 (not visible in FIG. 1) and a narrow side wall 12. An operating element 13 is located on the front wall 10. The connection cable 6 leading to the sensor is guided out at the lower narrow side wall of the housing 8. An attachment clip 14 is located on the upper narrow side of the housing, by means of which clip the evaluation apparatus 7 can for example be attached to the patient's clothes.

The evaluation apparatus 7 and the sensor 1 of the monitoring device A form an independent unit which communicates with the blood treatment device via a wireless connection. The monitoring device A will be described below together with the blood treatment device B with reference to FIG. 2, which schematically shows the essential components of the two devices.

In the embodiment, the blood treatment device B is a haemodialysis device comprising a dialyser 15, which is divided into a blood chamber 17 and a dialysate chamber 18 by a semipermeable membrane 16. An arterial hose line 20, which leads to the inlet of the blood chamber 17 of the dialyser 15, is connected to the patient's fistula or shunt (not shown) by means of an arterial cannula 19. A venous hose line 21, which is connected to the patient's fistula or shunt by means of a venous cannula 22, leads away from the outlet of the blood chamber 17 of the dialyser 15. A blood pump 23 is wired into the arterial hose line 20 and conveys the blood in the extracorporeal blood circuit I.

The dialysate circuit II of the dialysis device comprises a dialysate source 24, to which a dialysate feed line 25 is connected, which leads to the inlet of the dialysate chamber 18 of the dialyser 15. A dialysate removal line 26, which leads to an outlet 27, leads away from the outlet of the dialysate chamber 18 of the dialyser 15. A dialysate pump 28 is wired into the dialysate removal line 26.

A central control unit 29 takes on the control of the dialysis device and actuates the blood pump and dialysate pump 23, 28 via control lines 30, 31. The central control unit 29 is connected via a data line 32 to an alarm unit 33 which sets off an optical or acoustic alarm in the event of a fault.

An electromagnetically actuatable hose clamp 34, which is closed by the central control unit 29 via an additional control line 35 if the venous cannula 22 (needle) has slipped out of the vascular access, is located on the venous hose line 21 downstream of the blood chamber 17 of the dialyser 15. In addition, the control unit 29 stops the blood pump 23 after the cannula has slipped out. The slipping out of the cannula is detected by the monitoring device A, which communicates with the blood treatment device B via a wireless connection, preferably a radio connection. For this purpose, the blood treatment means B has a data transmission unit 36 which comprises a transmitting unit 36A and a receiving unit 36B.

The evaluation apparatus 7 of the monitoring means A comprises an evaluation unit 37 which evaluates the signal of the sensor 1 and generates a signal which is characteristic of the state of the vascular access, for example a signal which signals that the cannula has slipped out.

In order to produce the wireless connection to the data transmission unit 36 of the blood treatment device A, the evaluation apparatus 7 comprises a data transmission unit 38 which comprises a transmitting unit 38A and a receiving unit 38B. The two data transmission units 36, 38 form an interface which can operate according to the Bluetooth standard. If the cannula 22 has slipped out of the vascular access and the sensor 1 detects blood at the puncture site, the transmitting unit 38A of the evaluation apparatus 7 sends an alarm signal which is received by the receiving unit 36B of the blood treatment device B. Thereupon, the alarm unit 33 of the blood treatment device B sets off an acoustic and/or optical alarm and interrupts the blood treatment.

In addition, the evaluation apparatus 7 comprises a supervision unit 39 and a signalling unit 40. The supervision unit 39, which can be a component of the evaluation unit 37, monitors the wireless connection between the evaluation apparatus and blood treatment device. The signalling unit 40 comprises a vibration signal generator 40A. Signal generators of this type which generate vibrations belong to the prior art. They can comprise a motor, the motor shaft of which supports an imbalance. The vibration signal generator 40A is connected to the front and/or rear wall 10, 11 of the housing 8 of the evaluation apparatus 7, so that the entire housing is made to vibrate.

In the embodiment, the transmitting unit 36A of the blood treatment device B sends confirmation signals at particular time intervals if the receiving unit 36B of the blood treatment device receives signals from the transmitting unit 38A of the evaluation apparatus 7. The supervision unit 39 of the evaluation apparatus 7 continuously monitors the receipt of the confirmation signals. If the confirmation signals fail because the radio connection is disrupted, the supervision unit 39 generates a control signal, which the signalling unit 40 receives, so that the signalling unit activates the vibration signal generator 40A. However, in the embodiment, the supervision unit 39 only generates a control signal of this type when the wireless connection is interrupted for a period of time that is longer than a predetermined period of time. For this purpose, the supervision unit 40 can have an appropriate time function element. The period of time predetermined by the time function element should be designed such that mere brief position changes of the patient do not immediately lead to vibrations being triggered.

If the patient has laid on the evaluation apparatus 7, the supervision unit 40 immediately detects the interruption of the wireless connection. Thereupon, the monitoring unit 40 activates the vibration signal generator 40A of the signalling unit 40, which generator causes the housing to vibrate, and this is noticed by the patient even when said patient is asleep. The patient can then release the evaluation apparatus 7 again by assuming a different position, so that the connection is re-established.

When the connection is re-established, the confirmation signals are received again by the blood treatment device, upon which a conclusion is made regarding the re-establishment of the connection and the vibration signal is automatically deactivated. However, if the connection is not re-established or is interrupted again, the vibration signal is not deactivated and reactivated. An actuation member, such as a switch or button, can be provided on the evaluation apparatus for deactivating the vibration signal.

If the evaluation apparatus only sends data telegrams to the blood treatment device at particular time intervals, the vibration signal can only be deactivated automatically after a certain time delay. This can be avoided by the next data telegram being sent to the blood treatment device immediately after the patient has actuated an actuation member.

It is also possible for the transmitting unit 38A of the evaluation apparatus 7 to send a signal to the blood treatment device B once an interruption of the wireless connection has been detected, so that the blood treatment device sets off, by means of a signalling unit, an acoustic and/or optical signal which also signals to the medical staff that the radio connection has been interrupted. This acoustic or optical signal, however, is not sufficient by itself to wake the patient from their sleep; this, however, can be achieved with a higher degree of reliability with the vibration of the housing 8 of the evaluation apparatus 7, since according to research the patient reacts sensitively to vibrations on the body.

The invention claimed is:

1. A device for monitoring a vascular access for an extracorporeal blood treatment device having an extracorporeal blood circuit that comprises an arterial blood line having an arterial cannula and a venous blood line having a venous cannula, the device for monitoring the vascular access comprising:
   a sensor for detecting at least one physical variable that is characteristic of the state of the vascular access; and
   an evaluation apparatus that is connected to the sensor via a connection cable and comprises an evaluation unit for generating signals that are characteristic of the state of the vascular access including a signal that is characteristic of a faulty vascular state, the evaluation apparatus comprising a data transmission unit for producing a wireless connection between the evaluation apparatus and the blood treatment device,
   wherein the evaluation apparatus comprises a supervision unit and a signalling unit, the supervision unit being configured to detect an interruption of the wireless connection between the evaluation apparatus and the blood treatment device, the signalling unit being configured to give off a signal when the supervision unit detects the interruption of the wireless connection, the signalling unit comprising a vibration signal generator that uses vibrations to signal the interruption of the wireless connection, the evaluation apparatus comprising a flat housing having a front wall, a rear wall, and a narrow side wall, the vibration signal generator being connected to the front wall, the rear wall, or both, and the vibration signal generator comprising a motor, wherein the motor comprises a motor shaft configured to support an imbalance and generate vibration,
   wherein the supervision unit generates a control signal when the wireless connection is interrupted for a period of time that is longer than a predetermined period of time, the control signal being sent to the signalling unit to activate the vibration signal generator, and
   wherein the supervision unit comprises a time function element, the predetermined period of time being predetermined by the time function element, the predetermined period of time being designed such that mere brief positional changes of a patient do not immediately lead to vibrations.

2. The device according to claim 1, wherein the data transmission unit comprises a transmitting unit for sending the signals that are characteristic of the state of the vascular access to the blood treatment device, and a receiving unit for receiving confirmation signals from the blood treatment device, the monitoring unit being configured such that the monitoring unit detects when the receiving unit does not receive a confirmation signal from the blood treatment device signalling the existence of the wireless connection.

3. The device according to claim 1, wherein the data transmission unit is a unit that transmits radio signals or optical signals.

4. The device according to claim 1, wherein the sensor is designed as a pad that is made of flexible material and is to be placed on the patient's skin.

5. The device according to claim 1, wherein the sensor comprises a moisture or liquid sensor as the sensor element.

6. The device according to claim 1, wherein the connection cable is guided out of the housing at the narrow side wall.

7. An arrangement comprising a device for monitoring a vascular access, according to claim 1, and comprising an extracorporeal blood treatment device having an extracorporeal blood circuit that comprises an arterial blood line having an arterial cannula and a venous blood line having a venous cannula.

8. The arrangement according to claim 7, wherein the extracorporeal blood treatment device comprises a data transmission unit for producing a wireless connection between the blood treatment device and the evaluation apparatus.

9. The arrangement according to claim 8, wherein the data transmission unit of the blood treatment device comprises a transmitting unit for sending confirmation signals to the evaluation apparatus signalling the existence of the wireless connection and a receiving unit for receiving the signals that are characteristic of the state of the vascular access from the evaluation apparatus.

10. The arrangement according to claim 7, wherein the data transmission unit of the blood treatment device is a unit that transmits radio signals or optical signals.

11. The arrangement according to claim 7, wherein the blood treatment device comprises an alarm unit that is designed to generate an acoustic and/or optical signal after the wireless connection has been interrupted.

12. The arrangement according to claim 7, wherein the blood treatment device comprises an alarm unit that is designed to generate an acoustic and/or optical alarm following receipt of a signal that is characteristic of a faulty vascular access.

* * * * *